United States Patent [19]

Rittinger et al.

[11] Patent Number: 5,420,365
[45] Date of Patent: May 30, 1995

[54] PREPARATION OF 2,4-HEXADIYNE-1,6-DIOL

[75] Inventors: Stefan Rittinger, Ludwigshafen; Norbert Rieber, Mannheim, both of Germany

[73] Assignee: BASF Aktiengesellschaft, Germany

[21] Appl. No.: 176,825

[22] Filed: Jan. 3, 1994

[30] Foreign Application Priority Data

Jan. 22, 1993 [DE] Germany .................. 43 01 613.8

[51] Int. Cl.$^6$ .............................................. C07C 31/18
[52] U.S. Cl. ..................................................... 568/855
[58] Field of Search ......................................... 568/855

[56] References Cited

U.S. PATENT DOCUMENTS 2,232,867  2/1941  Reppe et al. .................... 568/855

FOREIGN PATENT DOCUMENTS 850153   8/1970  Canada .
725326   7/1942  Germany .
869053   3/1953  Germany .
877453   5/1953  Germany .
1174765  7/1964  Germany .
1906051  8/1970  Germany .
4137011  5/1993  Germany .

Primary Examiner—Howard T. Mars
Assistant Examiner—Rebecca Cook
Attorney, Agent, or Firm—John H. Shurtleff

[57] ABSTRACT

Process for the preparation of 2,4-hexadiyne-1,6-diol of the formula I $$HO-CH_2-CH_2-C \equiv C-C \equiv C-CH_2-OH \qquad (I)$$

by the reaction of diacetylene of the formula II $$H-C \equiv C-C \equiv C-H \qquad (II)$$

with formaldehyde of the formula III $$H_2C=O \qquad (III),$$

in the presence of a silver catalysts, in which the reaction is carried out in the presence of a polar organic solvent at temperatures ranging from 0° to 150° C. and under pressures ranging from 0.01 to 10 bar.

8 Claims, No Drawings

PREPARATION OF 2,4-HEXADIYNE-1,6-DIOL

The present invention relates to a process for the preparation of 2,4-hexadiyne-1,6-diol by the reaction of diacetylene with formaldehyde in the presence of a polar solvent and catalytic amounts of a silver catalyst.

DE-A 877,453 and DE-A 869,053 each disclose a process for the preparation of 2,4-hexadiyne-1,6-diol by the reaction of aqueous formaldehyde solution with diacetylene in the presence of Ag catalysts. Only low conversions of diacetylene are found when using an apparatus as described in Example 1 of DE-A 877,453 in a safe-to-handle dilution for diacetylene (DE-A 4,137,011) giving a very unsatisfactory reaction rate (comparative example A). The mode of operation described in DE-A 877,453 to improve the diacetylene yield (condensation and recycling of unconverted and degassed diacetylene) is impracticable on an industrial scale for reasons of safety.

It is thus an object of the present invention to overcome the aforementioned drawbacks.

Accordingly, we have found a novel and improved process for the preparation of 2,4-hexadiyne-1,6-diol of the formula I

HO-CH$_2$-C≡C-C≡C-CH$_2$-OH     (I), by the reaction of diacetylene of the formula II

H-C≡C-C≡C-H     (II), with formaldehyde of the formula III

H$_2$C=O     (III), in the presence of silver catalysts, wherein the reaction is carried out in the presence of a polar solvent at temperatures ranging from 0° to 150° C. and under pressures ranging from 0.01 to 10 bar.

The process of the invention can be carried out as follows:

The formaldehyde III, optionally in water or in aqueous solution (formalin solution), can be placed in a vessel with a polar solvent in the presence of from 0.001 to 5 wt % and preferably from 0.005 to 2 wt % and more preferably from 0.01 to 1 wt % of a silver catalyst, and the diacetylene bubbled into it at temperatures ranging from 0° to 150° C. and preferably from 20° to 130° C. and more preferably from 70° to 110° C. and pressures ranging from 0.01 to 1.4 bar and preferably from 0.1 to 1.2 bar and more preferably at atmospheric pressure (standard pressure).

Suitable silver catalysts usually comprise elementary, metallic silver or Ag⊕ salts, in particular silver or silver oxide on inert supports such as aluminum oxide or silicon dioxide.

The present process is particularly suitable for utilizing diacetylene-containing partial streams, such as commonly occur in industrial plant during separation of the cracked gas coming from the dissociation of hydrocarbons under the conditions of acetylene synthesis (Ullmann's Encycl. Of Indust. Chem., 5th Edition, A1, 1985). The mixtures of higher acetylenes (HA) which are formed partly as gas and partly as liquid can likewise be used in the process of the invention.

The gas mixture coming from the plant for working up cracked gas generally has an operating temperature which is slightly higher than ambient temperature. Preliminary separation, at ambient temperature, of readily condensable gaseous components in separating vessels disposed in the reactor inlet line improves the purity of the crude product.

The reaction may be carried out batchwise or, preferably, continuously in the gas phase or, preferably, in the liquid phase. Processes which are known to achieve good gas distribution in liquids, are advantageously used when using a gaseous partial stream, involving, for example, the use of equipment such as gassing rings, perforated trays, pressure-gassing equipment, spray reactors, or absorber towers. Suitable polar solvents are lactams, for example, pyrrolidones such as N-methylpyrrolidone, lactones, for example, lactones having 5 to 8 ring members such as butyrolactone, esters, for example, $C_1$-$C_{20}$ alkyl carboxylates such as methyl formate, methyl acetate, methyl propionate, ethyl formate, ethyl acetate and ethyl propionate, acid amides, for example, dialkyl formamides such as dimethyl-formamide, alcohols, for example, $C_1$-$C_{20}$ alkanols such as methanol and ethanol, alkylated ureas or glycol ethers such as ethylene glycol diethyl ether.

2,4-hexadiyne-1,6-diol I is one possible starting point for hexane-1,6-diol, which is an important intermediate for the production of polyesters, polyurethanes, adhesives, pharmaceuticals and textile auxiliaries.

EXAMPLES

The diacetylene in the stream of gas before and after the reaction was detected by gas chromatography on a packed column (20 % of Reoplex 400 on Chromosorb PAW) using N$_2$ as carrier gas (35 mL/min) and using FID detection. The concentrations are given in vol %. The concentration of the diacetylene as well as the content of substances in the product were determined using gas chromatography in liquid phase on a capillary column HP1 with the aid of a WLD detector.

EXAMPLE 1

A bubble-cap column having a diameter of 25 mm, a height of 1000 mm, and a glass frit (pore size 40 to 90 μm) for distributing the gas introduced at the bottom of the column was filled with a bed of 150 g of catalyst rings (13.7% of elementary Ag on α-Al$_2$O$_3$-rings) and with a mixture of 100 g of formalin (36% strength) and 100g of N-methylpyrrolidone (NMP). 20 L/h of HA (higher acetylenes) gas were passed into the solution at a reaction temperature of 95° C. Liquid components were condensed from the exhaust gas and recycled, dropwise, to the reaction. The concentration of hexadiyne diol rose as a linear function of time to a concentration of 9.3 vol % following a period of 10h, this corresponding to a space-time yield of approximately 15 g of product per kilogram of catalyst per hour. Due to the low residual concentration of formaldehyde (<5U%) the reaction rate then diminished. The average diacetylene depletion was approximately 10% during the first 30 hours of the experiment.

EXAMPLE 2

A bubble-cap column having a diameter of 25 mm, a height of 1000 mm, and a glass frit (pore size 40 to 90 μm) for distributing the gas introduced at the bottom of the column was filled with a bed of 150 g of catalyst rings (13.7% of elementary Ag on α-Al$_2$O$_3$-rings), and 200 g of the solvent mixture stated (formalin was used in each case in the form of a 36% strength solution) and 150 g of catalyst (the table below indicates the amount of active material and support material) were placed in the column and 20 L/h of HA gas were introduced at 95° C. The table lists the space-time yield of hexadiyne diol as a function of the solvent used for different catalysts.

TABLE

Yields of hexadiyne diol for various solvents

| Solvent Mixture | Ratio by volume | Catalyst | Space-time Yield [g product/kg (cat) · h] |
|---|---|---|---|
| water/hexane-1,6-diol | 1:1 | 15 wt % Ag/Al$_2$O$_3$ | 4 |
| water/butyrolactone | 1:1 | 15 wt % Ag/Al$_2$O$_3$ | 5 |
| water/ethylene glycol monomethyl ether | 1:1 | 15 wt % Ag/Al$_2$O$_3$ | 2 |
| water/N-methylpyrrolidone | 1:3 | 15 wt % Ag/Al$_2$O$_3$ | 5 |
| water/dimethylformamide | 1:1 | 15 wt % Ag/Al$_2$O$_3$ | 6 |
| water/N-methylpyrrolidone | 1:1 | 10 wt % Ag/SiO$_2$ | 15 |
| water/N-methylpyrrolidone | 1:1 | 5 wt % AgO$_2$/Al$_2$O$_3$ | 5 |

COMPARATIVE EXAMPLE A

A bubble-cap column having a diameter of 25 mm, a height of 1000 mm, and a glass frit (pore size 40 to 90 μm) for distributing the gas introduced at the bottom of the column was filled with a bed of 150 g of catalyst rings (13.7% of elementary Ag on α-Al$_2$O$_3$-rings). Following the addition of 150 g of formalin (content of formaldehyde 36%) 20 L/h of HA gas were passed into the solution at a reaction temperature of 95° C. Entrained liquid components were condensed from the exhaust gas and recycled, dropwise, to the reaction. During a reaction period of 30 h the maximum diacetylene depletion was 20%. The average depletion was less than 10%. During this period of time the concentration of hexadiyne diol (I) formed rose to 1.3 vol %, this being equivalent to a space-time yield of 0.45 g per kilogram of catalyst per hour.

We claim:

1. In a process for the preparation of 2,4-hexadiyne-1,6-diol by reacting diacetylene with formaldehyde, in the presence of a silver catalyst and water, at temperatures ranging from 0° to 150° C. and under pressures ranging from 0.01 to 10 bar, the improvement which comprises carrying out the reaction in the presence of a polar organic solvent and in a ratio by volume of water to polar organic solvent of from 1:1 to 1:3, said solvent selected from the group consisting of lactams, lactones, esters, acid amides, glycols and alkylated ureas.

2. A process as claimed in claim 1, wherein the polar organic solvent is selected from the group consisting of N-methylpyrrolidone, butyrolactone, dimethylformamide and hexane-1,6-diol.

3. A process as claimed in claim 1, wherein the polar organic solvent is N-methylpyrrolidone.

4. A process as claimed in claim 3, wherein the silver catalyst is metallic silver or silver oxide on an inert support and the reaction is carried out continuously over the supported catalyst.

5. A process for the preparation of 2,4-hexadiyne-1,6-diol I as claimed so in claim 1, wherein the reaction is carried out at temperatures ranging from 20° to 130° C.

6. A process for the preparation of 2,4-hexadiyne-1,6-diol I as claimed in claim 1, wherein the reaction is carried out at temperatures ranging from 70° to 110° C.

7. A process for the preparation of 2,4-hexadiyne-1,6-diol I as claimed in claim 1, wherein the reaction is carried out under pressures ranging from 0.1 to 1.5 bar.

8. A process for the preparation of 2,4-hexadiyne-1,6-diol I as claimed in claim 1, wherein the reaction is carried out at atmospheric pressure.

* * * * *